US011141419B1

(12) United States Patent
Kuchipudi

(10) Patent No.: US 11,141,419 B1
(45) Date of Patent: Oct. 12, 2021

(54) USE OF IMINOSUGARS AS PROPHYLACTIC AND THERAPY AGAINST COVID-19 / SARS-COV-2

(71) Applicant: The Penn State Research Foundation, University Park, PA (US)

(72) Inventor: Suresh Kuchipudi, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 17/241,894

(22) Filed: Apr. 27, 2021

Related U.S. Application Data

(60) Provisional application No. 63/017,307, filed on Apr. 29, 2020.

(51) Int. Cl.
| | |
|---|---|
| *A61K 31/702* | (2006.01) |
| *A61K 31/445* | (2006.01) |
| *A61P 31/14* | (2006.01) |
| *A61K 31/706* | (2006.01) |
| *A61K 31/437* | (2006.01) |

(52) U.S. Cl.
CPC .......... *A61K 31/702* (2013.01); *A61K 31/437* (2013.01); *A61K 31/445* (2013.01); *A61K 31/706* (2013.01); *A61P 31/14* (2018.01)

(58) Field of Classification Search
None
See application file for complete search history.

(56) References Cited

FOREIGN PATENT DOCUMENTS

WO    WO-2020185675 A1 * 9/2020 ........... A61K 31/336

OTHER PUBLICATIONS

Zhao, X., Guo, F., Comunale, M. A., Mehta, A., Sehgal, M., Jain, P., . . . & Guo, J. T. (2015). Inhibition of endoplasmic reticulum-resident glucosidases impairs severe acute respiratory syndrome coronavirus . . . Antimicrobial agents and chemotherapy, 59(1), 206. (Year: 2015).*
Alonzi, D. S., Scott, K. A., Dwek, R. A., & Zitzmann, N. (2017). Iminosugar antivirals: the therapeutic sweet spot. Biochemical Society Transactions, 45(2), 571-582. (Year: 2017).*
Ritchie, G. et al., Identification of N-linked carbohydrates from severe acute respiratory syndrome (SARS) spike glycoprotein, Virology, Feb. 2, 2010, vol. 399, pp. 257-269.
Durantel, D., Celgosivir, an alpha-glucosidase I inhibitor for the potential treatment of HCV infection, Current opinion in Investigational Drugs, 2009, vol. 10, No. 8, pp. 860-870.
Sung, C., et al., Extended Evaluation of Virological, Immunological and Pharmacokinetic Endpoints of CELADEN: A Randomized, Placebo-Controlled Trial of Celgosivir in Dengue Fever Patients, PLoS Neglected Tropical Diseases, Aug. 10, 2016, e0004851, pp. 1-23.
Warfield, K.L., et al., Lack of selective resistance of influenza A virus in presence of host-targeted antiviral, UV-4B, Scientific Reports, May 16, 2019, vol. 9, No. 7484, pp. 1-13.
Warfield, K.L., et al., Targeting Endoplasmic Reticulum alpha-Glucosidase I with a Single-Dose Iminosugar Treatment Protects against Lethal Influenza and Dengue Virus Infections, Journal of Medicinal Chemistry, Mar. 31, 2020, vol. 63, pp. 4205-4214.
Watanabe, S., et al., Optimizing celgosivir therapy in mouse models of dengue virus infection of serotypes 1 and 2: The search for a window for potential therapeutic efficacy, Antiviral Research, Jan. 13, 2016, vol. 127, pp. 10-19.
Rathore, A.P., et al., Celgosivir treatment misfolds dengue virus NS1 protein, induces cellular pro-survival genes and protects against lethal challenge mouse model, Antiviral Research, Oct. 12, 2011, vol. 92, pp. 453-460.

* cited by examiner

*Primary Examiner* — Dale R Miller
(74) *Attorney, Agent, or Firm* — Hodgson Russ LLP

(57) ABSTRACT

Provided are methods for prophylaxis or treatment of SARS-CoV-2 by administering a composition comprising one or more iminosugars to an individual in need thereof. The compositions may be administered to an individual who is at risk of becoming infected by SARS-CoV-2, or has been diagnosed with a SARS-CoV-2 infection. The iminosugars can inhibit SARS-CoV-2 cell entry and replication. The iminosugars potentiate co-administered antiviral agents, such as nucleoside analogs.

12 Claims, 5 Drawing Sheets

USE OF IMINOSUGARS AS PROPHYLACTIC AND THERAPY AGAINST COVID-19 / SARS-COV-2

CROSS-REFERENCE TO RELATED APPLICATIONS

This application claims priority to U.S. provisional patent application No. 63/017,307, filed Apr. 29, 2020, the entire disclosure of which is incorporated herein by reference.

STATEMENT REGARDING FEDERALLY SPONSORED RESEARCH OR DEVELOPMENT

This invention was made with government support under Hatch Act Project No. PEN04588 awarded by the United States Department of Agriculture. The government has certain rights in the invention.

BACKGROUND

The COVID-19 pandemic has created an unprecedented situation worldwide, which has not been experienced since the 1918 influenza pandemic. There are over 135 million confirmed cases worldwide and over 2.9 million deaths reported, with over one-quarter of cases from within the United States. The incubation period of SARS-CoV-2 infection is highly variable, ranging from 2-14 days or longer. Typically, COVID-19 causes flu-like symptoms including fever, malaise, muscle pain, and dry cough. This leads to shortening of breath, pneumonia, respiratory failure, septic shock, or multi-organ failure in severe cases, driven by an excessive inflammatory response. Due to the high basic reproductive number ($R_0$) and significant transmission during the asymptomatic phase of infection, control of the COVID-19 pandemic is very difficult.

Most current vaccines induce an immune response to the SARS-CoV-2 spike protein that mediates attachment to cells and is a major target of neutralizing antibodies. There is intense debate whether mutations in the spike glycoprotein facilitate escape from host antibodies and could potentially compromise vaccine effectiveness. Experimental co-incubation of live SARS-CoV-2 with highly neutralizing convalescent plasma resulted in the generation of a variant that is completely resistant to plasma neutralization in 80 days. SARS-CoV-2 continues to undergo antigenic evolution, and natural variants have already emerged with changes that could potentially allow immune escape. The United Kingdom reported a SARS-CoV-2 variant of concern (VOC), lineage B.1.1.7, also referred to as VOC 202012/01 or 20I/501Y.V1. The B.1.1.7 variant has subsequently been detected in over 30 countries and has been reported from 32 states in the USA. Phylogenetic analysis revealed that the B.1.1.7 variant has been circulating in the US. Another variant of SARS-CoV-2 (known as 20H/501Y.V2 or B.1.351) has emerged independently of B.1.1.7 in South Africa. This variant shares some mutations with B.1.1.7. Another variant of SARS-CoV-2 (known as P.1) emerged in Brazil and was detected in travelers during routine screening at Haneda airport outside Tokyo, Japan. The P1 variant has 17 unique mutations, including three in the receptor binding domain (RBD) of the spike protein. Cases attributed to B.1.351 and P.1 variants have also been reported in the US. Plasma from recipients of Moderna (mRNA-1273) or Pfizer-BioNTech (BNT162b2) vaccines was found to be significantly less effective in neutralizing SARS-CoV-2 variants encoding E484K or N501Y or the K417N:E484K:N501Y combination. A significant decrease in neutralizing titers against the B.1.351 but not the B.1.1.7 UK variant, with plasma from mRNA-1273 vaccinated humans and non-human primates has been reported. Therefore, there is a pressing need to develop interventions that are effective against both the currently circulating and future variants of SARS-CoV-2.

There are over 10 million immunocompromised people in the US, and there is evidence that SARS-CoV-2 infection of immunocompromised patients leads to persistent infection and accelerated viral evolution. The B.1.1.7 variant first discovered in the UK is believed to have originated due to evolution in a single chronically infected patient. In persistent infections, accelerated viral evolution was observed with predominant amino acid changes in the spike gene and the receptor-binding domain, which make up 13% and 2% of the viral genome, respectively, but harbored 57% and 38% of the observed changes. In the light of the continued evolution of SARS-CoV-2 and to protect older and immunocompromised individuals, effective prophylactics and therapeutics are still needed. A large global WHO solidarity study found that the repurposed drugs remdesivir, hydroxychloroquine, lopinavir, and interferon regimens had little or no effect on hospitalized COVID-19 patients. Combination therapies are suggested to alleviate patients from severe COVID-19 disease. Host-directed antiviral therapeutics provide an option as a combination therapy for these virus-targeted therapies, but there remains an ongoing and unmet need for additional approaches to prophylaxis and therapy for COVID-19. The present disclosure is pertinent to this need.

SUMMARY

The present disclosure provides compositions and methods for combating Coronavirus infections. The method is generally applicable to any infection caused by a member of the virus family Coronaviridae, examples of which include but are not necessarily limited to severe acute respiratory syndrome (SARS), Middle East respiratory syndrome (MERS), feline Coronavirus (FCoV) that can lead to the development of feline infectious peritonitis (FIP), and coronavirus disease 19 (COVID-19). In embodiments the individual to which a described composition is administered is a human, or a non-human animal.

In one embodiment, the disclosure provides a method for prophylaxis or treatment of a SARS-CoV-2 infection comprising administering to an individual in need thereof an effective amount of one or more iminosugars. In embodiments, the one or more iminosugars is selected from the group consisting of acarbose, miglitol, castanospermine, and combinations thereof. The disclosure further provides for co-administering an antiviral agent that is not an iminosugar. Results presented in this disclosure demonstrate that the iminosugar potentiates the effect of the antiviral agent, which in a non-limiting embodiment comprises Remdesivir. By using one or more iminosugars and optionally an additional antiviral compound, the method provides for at least one of: reducing SARS-CoV-2 virus entry into cells of the individual; reducing SARS-CoV-2 viral genome copy number in SARS-CoV-2 infected cells of the individual; and preventing death of cells infected by SARS-CoV-2. The method is expected to be effective against any SARS-CoV-2 virus, including known and hereafter arising variants, the known variants including the P.1 variant, the B.1.1.7 variant, and the B.1.351 variant. The compositions may be administered to an individual is at risk of contracting a SARS-

BRIEF DESCRIPTION OF THE FIGURES

FIG. 2. Iminosugars reduce SARS-CoV-2 viral genome copy number and viable virus output during infection in Vero E6 cells. Vero E6 cells were infected with SARS-CoV-2 virus at a multiplicity of infection (MOI) of 0.01. These infected cells were treated with 100 µM of iminosugars for 24 hrs. Later, the cell culture supernatant was collected and assayed for (A) viral genome copy number and (B) viable virus output. Significant reduction in the viral genomic copy number (SARS-CoV-2 N1 gene PCR) and viable virus ($TCID_{50}$/mL) output was observed with iminosugar treated virus wells. Data shown are Mean±SD of triplicates. *$p<0.05$, $p<0.01$, *$p<0.001$, ****$p<0.0001$ by Dunnett's multiple comparison test (ANOVA).

FIG. 4. Iminosugars potentiate the anti-viral effect of Remdesivir. The antiviral effect of 100 µM of Remdesivir was compared against 50 µM of Remdesivir potentiated with 50 µM of individual iminosugars. Vero E6 cells were infected with SARS-CoV-2 virus at an MOI of 0.01 and then treated with either Remdesivir or Remdesivir and Iminosugar combinations for 24 hrs. The cell culture supernatant was tested for viral genome copy number by qPCR (SARS-CoV-2 N1 gene). The antiviral effect of Remdesivir, was potentiated significantly when iminosugars were added, both against (A) SARS-CoV-2/WA/1 isolate and (B) variant of concern SARS-CoV-2/B.1.1.7. Data shown are Mean±SD of triplicates. ****$p<0.0001$ by Dunnett's multiple comparison test (ANOVA).

DESCRIPTION OF THE DISCLOSURE

Figure 1:
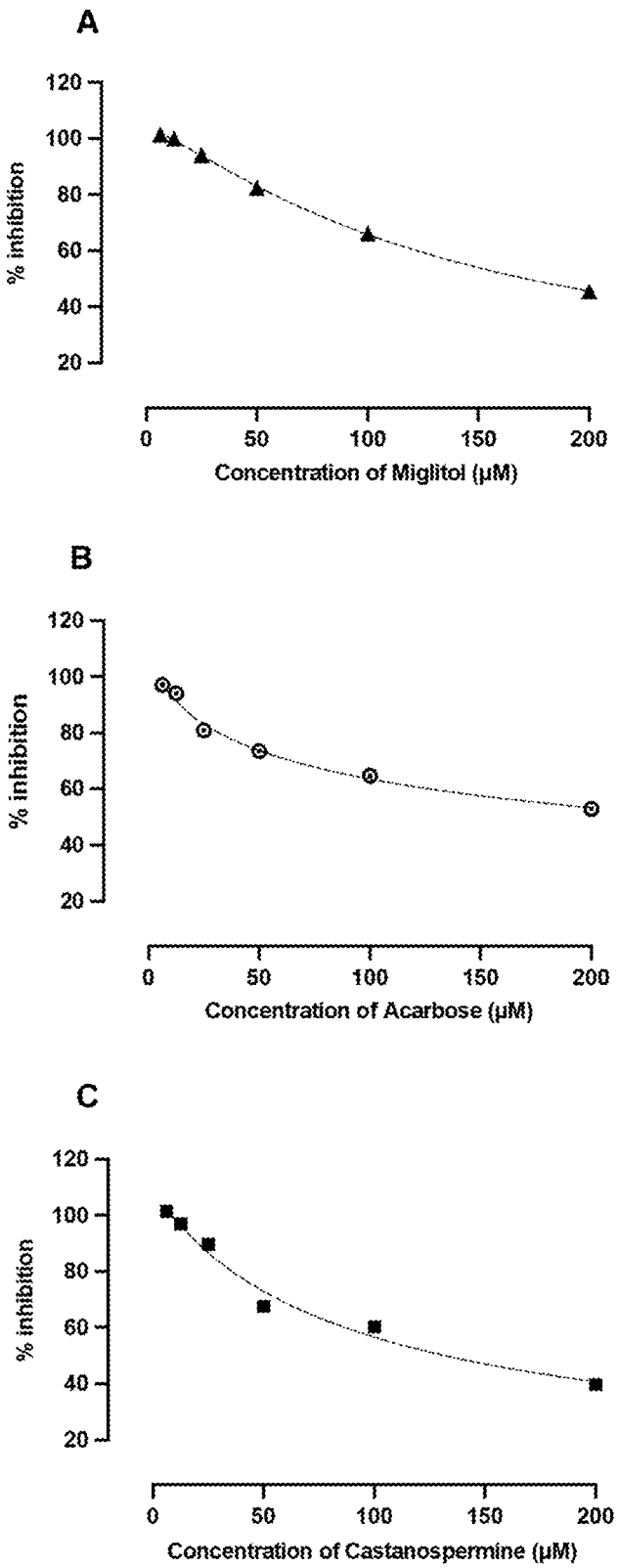
FIG. 1. Treatment of VeroE6 cells with iminosugars inhibits SARS-CoV-2 plaque formation. Vero E6 cells were pre-treated with various concentrations of iminosugars and infected with 40 plaque forming units (PFU) of SARS-CoV-2/WA/1 virus. Post infection, the virus was removed, and the cells were overlaid with cellulose semi-solid medium mixed with iminosugars (similar concentrations as pre-treatment). The cells were fixed post 48 hrs and stained with formaldehyde-crystal violet solution. The plaques were counted, and the percent inhibition was calculated with the formula [(PFU in iminosugar treated wells×100)/(PFU in virus controls)]. A non-linear dose-response curve was fit to the resulting average percent inhibition and the $IC_{50}$ values were determined. The $IC_{50}$ for Miglitol (A), Acarbose (B) and Castanospermine (C) against SARS-CoV-2 was 134.9, 105.1 and 90.98 µM respectively. The data represented is from duplicate wells.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

In certain aspects the disclosure includes use of iminosugars as further described herein, and includes pharmaceutical formulations comprising at least one iminosugar. In embodiments, compositions comprising one or more iminosugars are administered to an individual in need thereof for prophylaxis and/or therapy of a Coronavirus infection. In embodiments, the method can be used for any member of the virus family Coronaviridae, including but not necessarily limited to any Coronavirus that that causes any of severe acute respiratory syndrome (SARS), Middle East respiratory syndrome (MERS), coronavirus disease 19 (COVID-19) or feline Coronavirus (FCoV) that can lead to the development of feline infectious peritonitis (FIP). Thus, the disclosure is relevant for use with humans, and also for non-human animals, such as for veterinary purposes. In embodiments, the disclosure is pertinent to prophylaxis and therapy for infections caused by SARS-CoV-2. The compositions and methods are thus related to preventing or treating COVID-19.

In relation to the presently provided approaches, iminosugars are polyhydroxylated secondary and tertiary amines which resemble monosaccharide sugars. The ring oxygen is replaced by nitrogen. It is considered that any one or combination of iminosugars can be used in the methods of this disclosure. In embodiments, an iminosugar used in a method of this disclosure is any compound described in Biochem Soc Trans. 2017 Apr. 15; 45(2): 571-582, the disclosure of which is incorporated herein by reference. In non-limiting embodiments, the iminosugar comprises a compound that is a competitive inhibitor of an enzyme that act on a sugar substrate. In embodiments, the iminosugar is a monocyclic or bicyclic iminosugar. In embodiments, the iminosugar is N-(9'-methoxynonyl)-1-deoxynojirimycin (MON-DNJ), N-(6'-4"-azido-2"-nitrophenylamino) hexyl-1-deoxynojirimycin (NAP-DNJ), N-butyl-deoxynojirimycin (NB-DNJ), or N-nonyl-deoxynojirimycin (NN-DNJ). In embodiments, the iminosugar is acarbose, miglitol, castanospermine, or a combination thereof.

In embodiments, suitable pharmaceutical compositions can be prepared by mixing one or more iminosugars described herein with a pharmaceutically acceptable carrier, diluent or excipient, or immune response regulator, and suitable such components are well known in the art. Some examples of such carriers, diluents and excipients can be found in: Remington: The Science and Practice of Pharmacy 23rd edition (2020), the disclosure of which is incorporated herein by reference. In embodiments, iminosugars can be combined with a carrier in any suitable manner, e.g., by admixture, solution, suspension, emulsification, encapsulation, absorption and the like, and can be made in formulations such as tablets, capsules, powder (including lyophilized powder). In an embodiment, one or more than one iminosugars described herein may be the only anti-viral compound(s) present in the pharmaceutical formulation.

Administration of compositions as described herein can be performed using any suitable route of administration, including but not limited to parenteral, intraperitoneal, intrapulmonary, and oral administration, the latter including but not limited to intranasal administration. In embodiments, the composition is administered orally. In embodiments, the administration is such that an iminosugar can access the lungs of an individual, and thus inhalation of the described compositions is included. In an embodiment, a composition of the disclosure is suitable for nebulization for inhaled delivery to the lungs. In embodiments, for prophylactic uses, the compositions may be administered orally. For those with active COVID-19, including but not necessarily limited to individuals who are hospitalized and have COVID-19, the disclosure includes administration using nebulization of the compositions, such as for inhalation.

In embodiments, an effective amount of one or more sugars described herein is administered. An effective amount means an amount effective to inhibit viral infection, and/or inhibit the onset of one or more symptoms of COVID-19, and/or reduce the severity of any such symptoms, and/or lessen the duration of the condition. In embodiments, an effective amount is amount of the iminosugar sufficient to prevent, or reduce by at least about 30 percent, or by at least 50 percent, or by at least 90 percent, any sign or symptom of SARS-CoV-2 infection. In embodiments, fever is prevented or is less severe than if the iminosugar had not been administered to an infected individual. In embodiments, viral pneumonia is inhibited or prevented in an infected individual. In embodiments, transmission of the virus from an infected individual to a non-infected individual is inhibited or prevented. Accordingly, administering a composition of the disclosure can reduce infectivity of an individual, and thereby reduce SARS-CoV-2 spread in a population by limiting the amount of viral particles produces by infected individuals who received the iminosugar. In embodiments, an effective amount of an iminosugar comprises 25-50 mg administered orally three times per day.

In embodiments, administration of one or more iminosugars as described herein inhibits SARS-CoV-2 cell entry, and/or SARS-CoV-2 replication. In embodiments, administration of one or more iminosugars as described herein prevents lethality of the SARS-CoV-2 infection, or reduces the time an individual with a SARS-CoV-2 infection is on a ventilator, or prevents the infection from progressing to a severity such that a ventilator is used. In embodiments, the one-or more iminosugar administration is not toxic to the individual. In embodiments, administration of one or more iminosugars inhibits or prevents an increase in inflammatory cytokines in an individual infected with SARS-CoV-2.

In embodiments, the individual is a human and is of an age wherein risk of developing and/or experiencing adverse outcomes due to having COVID-19 is heightened, such as any individual over the age of 50 years. In embodiments, the individual has an underlying condition wherein the risk of developing severe symptoms of COVID-19, is increased, including but not necessarily limited to any respiratory condition. In embodiments, the individual is an adult human, an adolescent human, a child, or an infant. In embodiments, the individual is a male or female human. In embodiments, a composition comprising one or more iminosugars as described herein is administered to an individual who is not in need of the described iminosugars for a reason other than prophylaxis and/or therapy of SARS-CoV-2 infection. In embodiments, the individual does not have cystic fibrosis, diabetes, Niemann-Pick type C disease, Gaucher disease, Fabry disease, a lysosomal storage disorder, or a viral infection other than SARS-CoV-2, including but not necessarily limited to any influenzas and any other SARS virus.

In embodiments, a prophylactic or therapeutic effect of the disclosure can be compared to a suitable control. In embodiments, the prophylactic or therapeutic effect comprises an effect measured using cells that are exposed to SARS-CoV-2 and are not exposed to an iminosugar as described herein, or are exposed to an antiviral agent that is not an iminosugar and is used as a pharmaceutical monotherapy. Use of combinations of the described iminosugar and any other anti-viral agents, and/or immune modulators, are accordingly included in the scope of this disclosure.

In embodiments, administering one or more iminosugars includes co-administering a different antiviral agent. In embodiments, the co-administered iminosugar(s) potentiates the efficacy of a co-administered antiviral agent. The co-administered agent can be administered concurrently or sequentially with the one or more iminosugars. Thus, the disclosure provides for a synergistic prophylactic and/or therapeutic antiviral effect when combining a described iminosugar with a different anti-viral agent. For example, in embodiments, one or more iminosugars as described herein can be used in combination with one or more different antiviral compounds, non-limiting example of which includes nucleoside analogs such as Remdesivir and Galidesivir, to thereby enhance the efficacy of the anti-viral compound(s). In a non-limiting embodiment, enhancing, e.g., potentiating, the effect of a co-administered antiviral agent comprises a reduction in viral copy number in SARS-CoV-2 infected cells that is greater than the reduction in viral copy number achieved by administering the antiviral agent without the iminosugar. Accordingly, the disclosure provides improved therapeutic approaches.

In embodiments, one or more described iminosugars reduce SARS-CoV-2 virus entry into human cells. Accordingly, the disclosure provides an improved prophylactic approach. Data presented in this disclosure also demonstrates that the described iminosugars can inhibit viral entry of SARS-CoV-2 variants, such as P.1, B.1.1.7, B.1.351. Thus, it is expected that the described approaches will be broadly applicable in inhibiting viral entry of these and other SARS-CoV-2 variants that may emerge in the future.

In embodiments, one or more iminosugars as described herein are administered in conjunction with a steroid, including but not necessarily limited to a corticosteroid. In embodiments, the steroid is dexamethasone, prednisolone, methylprednisolone, or ciclesonide.

In embodiments, one or more iminosugars as described herein are administered in conjunction with one or more protease inhibitors, such as lopinavir and ritonavir.

In embodiments, one or more iminosugars as described herein are administered in conjunction with Favipiravir, Ribavirin, or hydroxychloroquine.

In embodiments, one or more iminosugars as described herein are administered in conjunction with a therapeutic or prophylactic antibody composition. In embodiments, the antibody composition comprises Tocilizumab. In embodiments, the therapeutic antibody composition comprises polyclonal or monoclonal antibodies that bind to one or more SARS-CoV-2 epitopes. In embodiments, the antibodies are from or derived from SARS-CoV-2 convalescent patient serum. In embodiments, the antibodies comprise $V_H H$ single chain antibodies. In embodiments, the antibodies comprise SARS-CoV-2 neutralizing antibodies. In embodiments, a plurality of antibodies that bind to one or more SARS-CoV-2 escape mutants are administered.

In embodiments, one or more iminosugars as described herein are administered in conjunction with a SARS-CoV-2 vaccine, including but not necessarily limited to nucleic acid based vaccines, adenovirus-based vaccines, and protein-based vaccines.

The disclosure provides results showing that several representative iminosugars are effective against SARS-Co-V2 using relevant cell types. Results include data obtained using monkey VeroE6 cells and Huh7.0 cells. The data, as discussed further below in the Examples and as illustrated in the Figures, demonstrate that iminosugars can inhibit SARS-CoV-2 plaque formation, reduce SARS-CoV-2 viral genome copy number and viable virus output during infection, reduce SARS-CoV-2 virus entry into human cells, potentiate the effect of virus-targeted anti-viral drugs, and moreover, inhibit cell death caused by SARS-CoV-2 infection. Each of these effects is encompassed by the methods of this disclosure.

The following Examples are intended to illustrate various embodiments of the disclosure, but are not intended to be limiting.

Example 1

Figure 2:
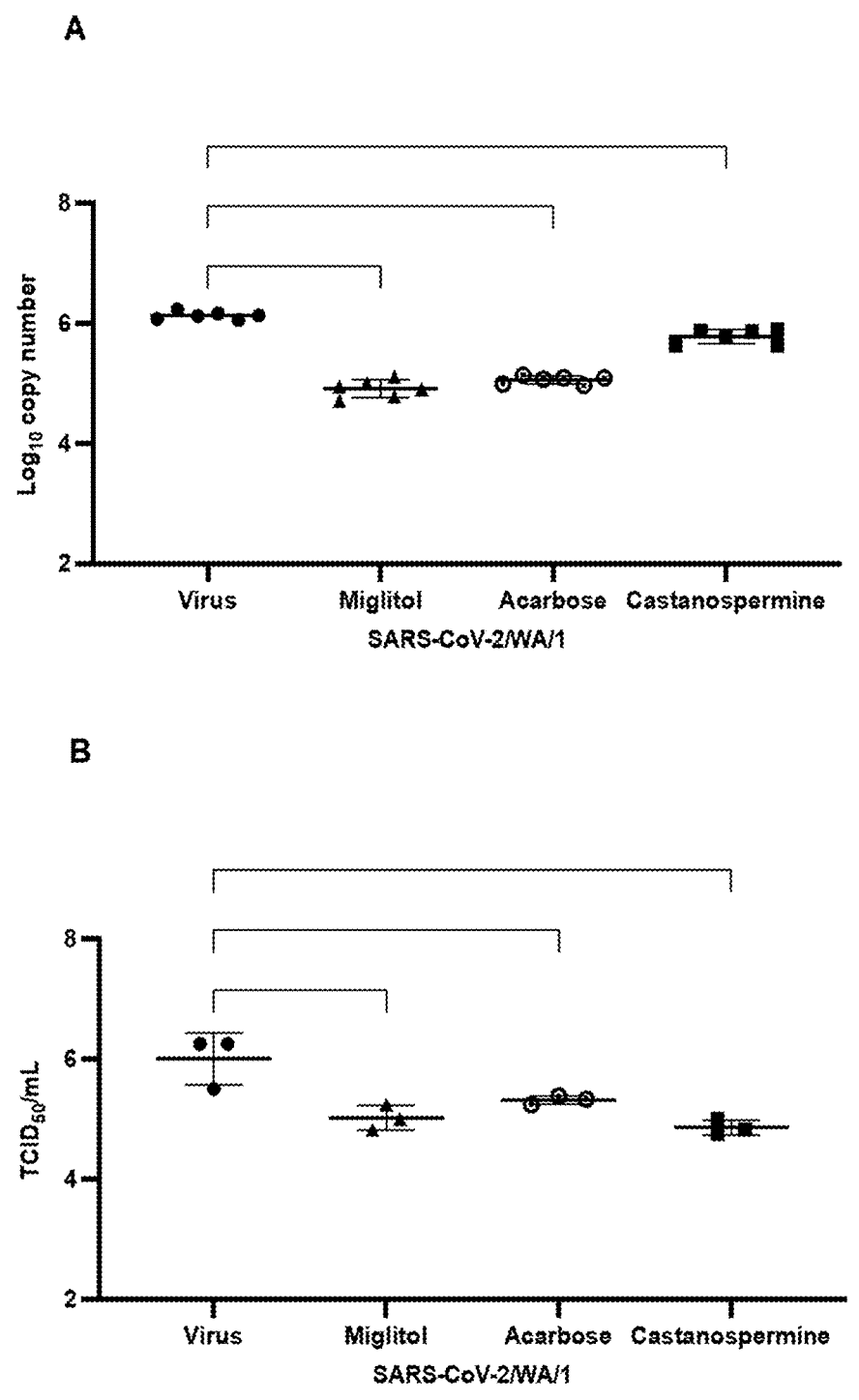

This Example demonstrates that Iminosugar treatment significantly reduces SARS-CoV-2 replication in Vero E6 cells. We analyzed iminosugars acarbose, miglitol and castanospermine as antivirals against SARS-CoV-2 in monkey VeroE6 cells. A plaque reduction assay demonstrated a dose-dependent inhibition or reduction of SARS-CoV-2 plaques. Cells were treated with iminosugars prior and post-infection with SARS-CoV-2. The half maximal inhibitory concentration ($IC_{50}$) was calculated from resulting number of plaques per each concentration of the tested iminosugars (FIG. 1). SARS-CoV-2 viral RNA production was significantly reduced in cells treated with miglitol, acarbose, or castanospermine (FIG. 2A). Correspondingly, SARS-CoV-2 infectious titers from cell culture supernatants were reduced by 0.5-1.5 logo in iminosugar-treated cells compared with vehicle treated control cells (FIG. 2B).

Example 2

This Example demonstrates that iminosugar treatment significantly reduces SARS-CoV-2 and its variants' entry in human cells.

Figure 3:
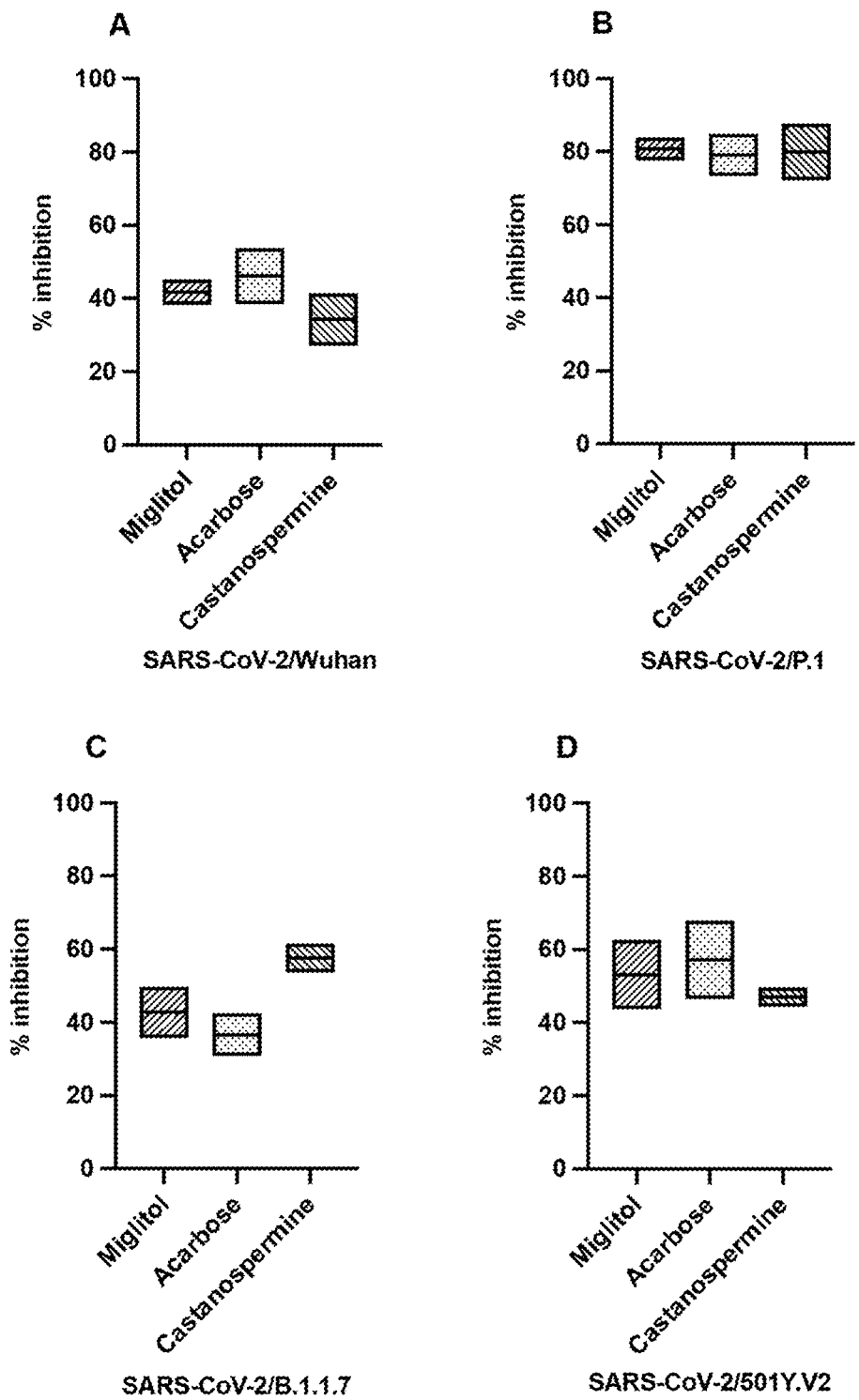
FIG. 3. Iminosugars reduce pseudotyped SARS-CoV-2 virus entry into human cells. 293t-hACE2 cells were treated with 100 µM of iminosugars for 24 hrs. Later, these cells were inoculated with pseudoviruses (Lentiviruses expressing SARS-CoV-2 spike proteins and a luciferase reporter), along with iminosugars. Lentiviruses individually expressing spike glycoprotein of SARS-CoV-2 (A) Wuhan isolate and variants of concern-(B) P.1, (C) B.1.1.7, (D) B.1.351 were tested. After 48 hrs, the treated cells were lysed and assayed for luciferase activity. Percent inhibition was calculated as [(LU in iminosugar treated wells×100)/(LU in virus controls)]. The data represented is from duplicate wells.

We assayed the ability of iminosugars to limit viral entry of SARS-CoV-2 and its variants. Pseudoviruses were generated which expressed the spike glycoprotein of SARS-CoV-2 and variants of concern—P.1, B.1.1.7, B.1.351. Treatment with miglitol, acarbose or castanospermine caused significant decrease in pseudotyped SARS-CoV-2 viral entry into human 293t-hACE2 cells (FIG. 3).

Example 3

This Example demonstrates that Iminosugars potentiate the effect of virus-targeted anti-viral drugs.

Figure 4:
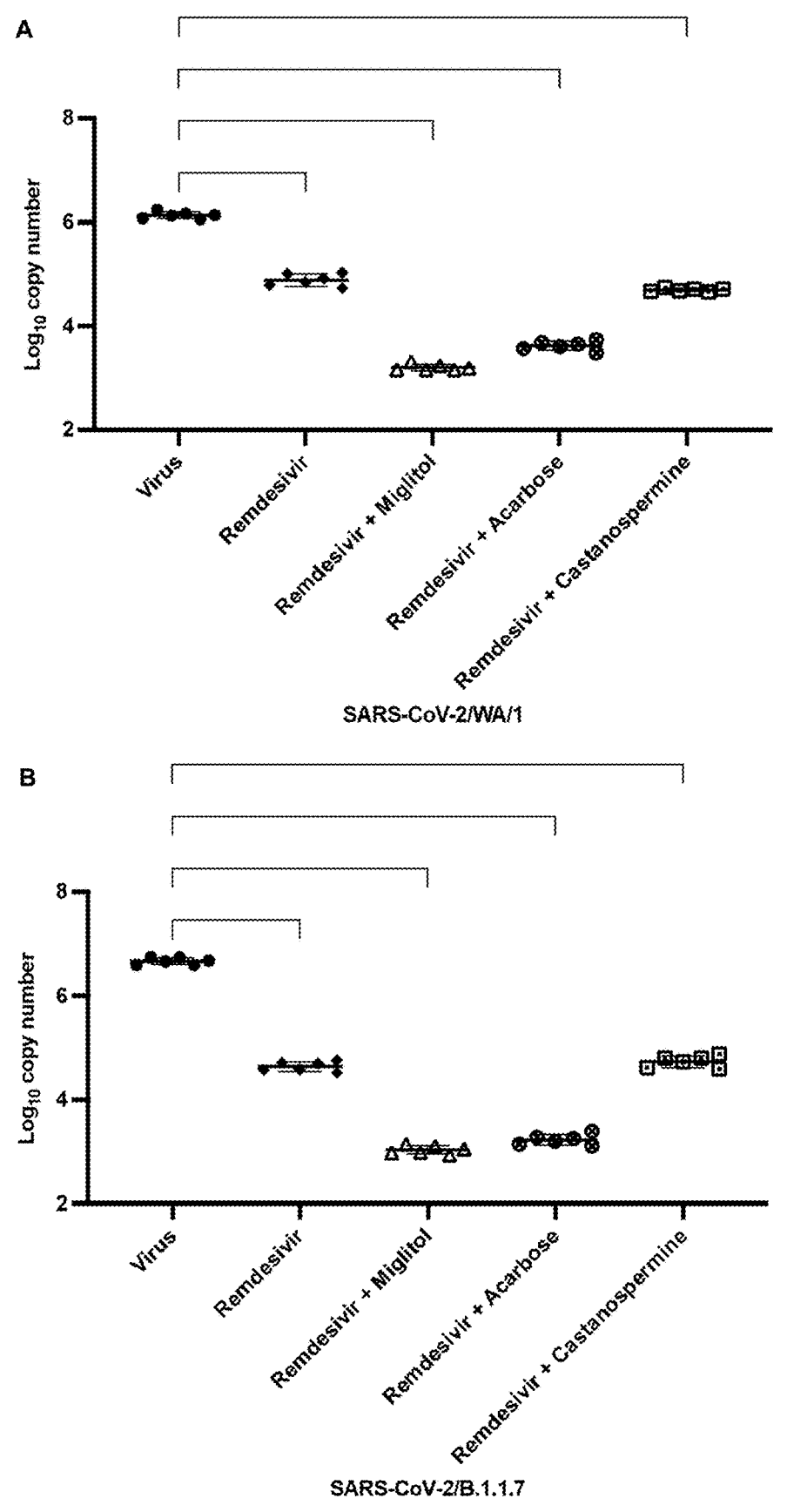

There are several virus targeted anti-viral drugs being tested to treat SARS-CoV-2 infection. There are contradictory reports on the efficacy of these anti-viral drugs for treatment of COVID-19 patients. We performed tests to determine if the iminosugars potentiated the effect of these virus targeted therapeutics. Remdesivir is a nucleoside analogue, which has shown to be effective in alleviating the symptoms of severe COVID-19 patients. The data show that the anti-viral effect of Remdesivir is significantly potentiated by addition of the iminosugars (FIG. 4).

Example 4

This Example demonstrates that acarbose and miglitol prevent cell death caused by SARS-CoV-2 infection.

Figure 5:
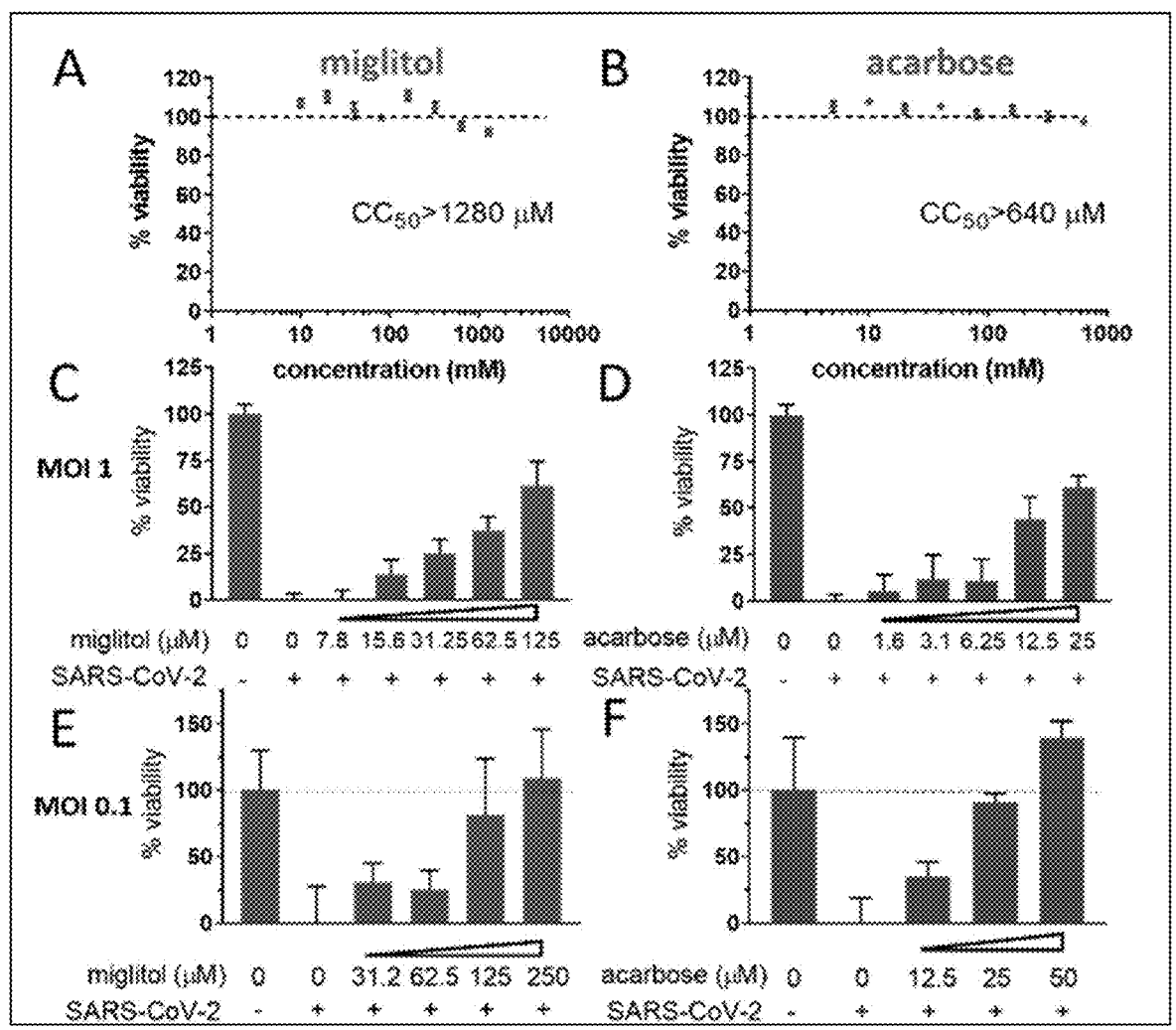
FIG. 5. Acarbose and miglitol reduce death of human cells during infection with SARS-Co-V2 without toxicity. Huh7.0 human cells were grown in the presence of various concentrations of miglitol (A, C, E) or acarbose (B, D, F) and remained uninfected (A, b) or were infected with SARS-CoV-2 at MOI 1 (C, D) or 0.1 IE, F). After three days, cell viability measured by MTS assay was calculated as percent of uninfected cell viability (100%) normalized to no-drug control cell viability (0%). Data shown are mean±of three replicates.

Infection with SARS-CoV-2 causes necrotic damage to tracheobronchial tissue, bronchioles, and lungs, with diffuse alveolar damage and other tissue damage evident at early stages of symptomatic infection. Several reports have also noted tissue damage due to cell death in various extrapulmonary tissues including heart, brain, liver, spleen and tissues of the gastrointestinal tract. Cell death during infection is associated with activation of the NLRP3 inflammasome, which leads to inflammation. Dysregulated proinflammatory cytokine response frequently referred as "cytokine storm" is evident in patients with severe COVID-19. Therefore, we analyzed whether iminosugars could limit cell death in SARS-CoV-2 infected Huh7.0 cells. At a high multiplicity of infection (MOI), improvement of cell survival was achieved with low concentrations of iminosugars, and over 50% of viral-induced cell death was reversed with 125 µM miglitol or 25 µM acarbose (FIGS. 5C&D). At lower MOI, cell survival was completely restored with 250 µM miglitol or 50 µM acarbose (FIGS. 5E&F). This is strong evidence that iminosugar antiviral therapy may reduce tissue damage caused by cell death from SARS-CoV-2 infection and thus reduce morbidity.

While the disclosure has been particularly shown and described with reference to specific embodiments, it should be understood by those having skill in the art that various changes in form and detail may be made therein without departing from the spirit and scope of the present disclosure as disclosed herein.

What is claimed is:

1. A method for treatment of or to inhibit the onset of a SARS-CoV-2 infection comprising administering to an individual in need thereof an effective amount of a composition comprising one or more iminosugars, selected from the group consisting of acarbose, miglitol, castanospermine and a combination thereof, and Remdesivir, wherein the one or more iminosugars potentiates the effect of Remdesivir.

2. The method of claim 1, wherein the administering reduces SARS-CoV-2 virus entry into cells of the individual.

3. The method of claim 2, wherein the SARS-CoV-2 virus is a P.1 variant, a B. 1.1.7 variant, or a B. 1.351 variant.

4. The method of claim 1, wherein the administering reduces SARS-CoV-2 viral genome copy number in SARS-CoV-2 infected cells of the individual.

5. The method of claim 1, wherein the administering reduces death of cells infected by SARS-CoV-2.

6. The method of claim 1, wherein the individual is at risk of contracting the SARS-CoV-2 infection.

7. The method of claim 1, wherein the individual is suspected of having or has been diagnosed with the BARS-CoV-2 infection.

8. The method of claim 1, wherein the individual has been diagnosed with the SARS-CoV-2 infection.

9. The method of claim 8, wherein the administering reduces BARS-CoV-2 viral genome copy number in BARS-CoV-2 infected cells of the individual.

10. The method of claim 8, wherein the iminosugar is acarbose.

11. The method of claim 8, wherein the iminosugar is miglitol.

12. The method of claim 8, wherein the iminosugar is castanospermine.

* * * * *